(12) United States Patent
Kim et al.

(10) Patent No.: US 11,191,494 B2
(45) Date of Patent: Dec. 7, 2021

(54) HEALTHCARE DEVICE AND VEHICLE SYSTEM INCLUDING THE SAME

(71) Applicants: Hyundai Motor Company, Seoul (KR); Kia Motors Corporation, Seoul (KR)

(72) Inventors: Gyun Ha Kim, Incheon (KR); Eung Hwan Kim, Seoul (KR); Sang Kyung Seo, Seoul (KR); Dae Yun An, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 8 days.

(21) Appl. No.: 16/597,501

(22) Filed: Oct. 9, 2019

(65) Prior Publication Data
US 2021/0007679 A1  Jan. 14, 2021

(30) Foreign Application Priority Data
Jul. 12, 2019  (KR) .................. 10-2019-0084433

(51) Int. Cl.
*A61B 5/00* (2006.01)
*H04Q 9/00* (2006.01)
(Continued)

(52) U.S. Cl.
CPC .............. *A61B 5/746* (2013.01); *A61B 5/339* (2021.01); *A61B 5/7405* (2013.01);
(Continued)

(58) Field of Classification Search
CPC ... A61B 2560/0204; A61B 5/25; A61B 5/339; A61B 5/6893; A61B 5/7225; A61B 5/7405; A61B 5/7455; A61B 5/746; A61B 5/044; A61B 5/02055; A61B 5/165; A61B 2560/0219; B60R 16/023; B60R 16/03; B60R 11/02; B60R 2011/0012; B60R 2011/0007; B60W 2040/0872; B60W 50/08; G09G 3/3208; H04L 67/12;
(Continued)

(56) References Cited

U.S. PATENT DOCUMENTS

2014/0347082 A1 * 11/2014 Jeong ................. G01R 1/06772
324/750.27
2015/0230019 A1 *  8/2015 Sakai ................... H04R 1/1041
381/74
(Continued)

*Primary Examiner* — Sisay Yacob
(74) *Attorney, Agent, or Firm* — Mintz Levin Cohn Ferris Glovsky and Popeo, P.C.; Peter F. Corless

(57) ABSTRACT

A healthcare device and a vehicle system are capable of charging a sensor device that measures a biosignal. The healthcare device includes the sensor device that includes a biosignal measuring sensor that measures the biosignal and uses the biosignal measuring sensor as a charging electrode during charging, a healthcare controller that collects and calculates the biosignal measured through the biosignal measuring sensor, a sensor device battery that receives power from an external pogo pin through an electrode of the biosignal measuring sensor during charging by the charging electrode to charge a power supply of the sensor device battery, and a selecting device that connects the biosignal measuring sensor to any one of the healthcare controller and the sensor device battery.

14 Claims, 12 Drawing Sheets

(51) Int. Cl.
   *H04L 29/08* (2006.01)
   *G09G 3/3208* (2016.01)
   *A61B 5/044* (2006.01)
   *B60R 16/023* (2006.01)
   *B60R 16/03* (2006.01)
   *A61B 5/339* (2021.01)

(52) U.S. Cl.
   CPC .......... *A61B 5/7455* (2013.01); *B60R 16/023* (2013.01); *B60R 16/03* (2013.01); *G09G 3/3208* (2013.01); *H04L 67/12* (2013.01); *H04Q 9/00* (2013.01); *H04Q 2209/88* (2013.01)

(58) Field of Classification Search
   CPC ....... H04Q 2209/88; H04Q 9/00; H02J 50/10; H02J 50/60; H02J 7/00; B60K 35/00
   See application file for complete search history.

(56) References Cited

U.S. PATENT DOCUMENTS

2016/0038083 A1\* 2/2016 Ding .................... A61B 5/1121
  600/388
2018/0212449 A1\* 7/2018 Park ...................... H02J 7/0042
2019/0357796 A1\* 11/2019 Tanaka ...................... H02J 7/00

\* cited by examiner

HEALTHCARE DEVICE AND VEHICLE SYSTEM INCLUDING THE SAME

CROSS-REFERENCE TO RELATED APPLICATION

This application claims under 35 U.S.C. § 119(a) the benefit of Korean Patent Application No. 10-2019-0084433, filed in the Korean Intellectual Property Office on Jul. 12, 2019, the entire contents of which are incorporated herein by reference.

BACKGROUND

(a) Technical Field

The present disclosure relates to a healthcare device and a vehicle system including the same, more particularly, to the healthcare device and vehicle system capable of charging a sensor device that measures a biosignal.

(b) Description of the Related Art

In conjunction with trends such as aging of the population, income inequality, and the spread of wellness culture, the medical paradigm is shifting from treatment to prevention and management. Accordingly, the healthcare industry is attracting increased attention worldwide.

Recently, a driver assistance system for assisting a driver when driving a vehicle has been developed. In particular, as interest in health increases, certain biometric information of the driver may be collected through a healthcare device provided in the vehicle.

The driver assistance system applies the healthcare device to the vehicle and collects the biometric information of the driver by using a connected or contactless sensor. Accordingly, a corresponding operation may be performed according to the biometric state of a user who is in the vehicle.

The healthcare device charges the sensor device using a separate pogo pin. Thus, an existing healthcare device requires a charging pin connected to the pogo pin on the outside of the device, thereby negatively affecting the aesthetic value of its appearance.

SUMMARY

An embodiment of the present disclosure uses a biosignal measuring sensor as a charging electrode when charging a sensor device for measuring a biosignal.

In addition, an embodiment of the present disclosure uses a biosignal measuring sensor as a charging electrode when a sensor device is charged in a vehicle device interconnected with a healthcare device.

According to an aspect of the present disclosure, a healthcare device includes a sensor device that includes a biosignal measuring sensor that measures a biosignal and uses the biosignal measuring sensor as a charging electrode during charging, a healthcare controller that collects and calculates the biosignal measured through the biosignal measuring sensor, a sensor device battery that receives power from an external pogo pin through an electrode of the biosignal measuring sensor during charging by the charging electrode to charge a power supply of the sensor device battery; and a selecting device that connects the biosignal measuring sensor to any one of the healthcare controller and the sensor device battery.

According to another aspect of the present disclosure, a vehicle system includes a healthcare device that measures a biosignal corresponding to user information through a biosignal measuring sensor and charges a sensor device battery using the biosignal measuring sensor as a charging electrode during charging, and a vehicle device connected to the healthcare device through a communication network to transfer the user information to the healthcare device.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
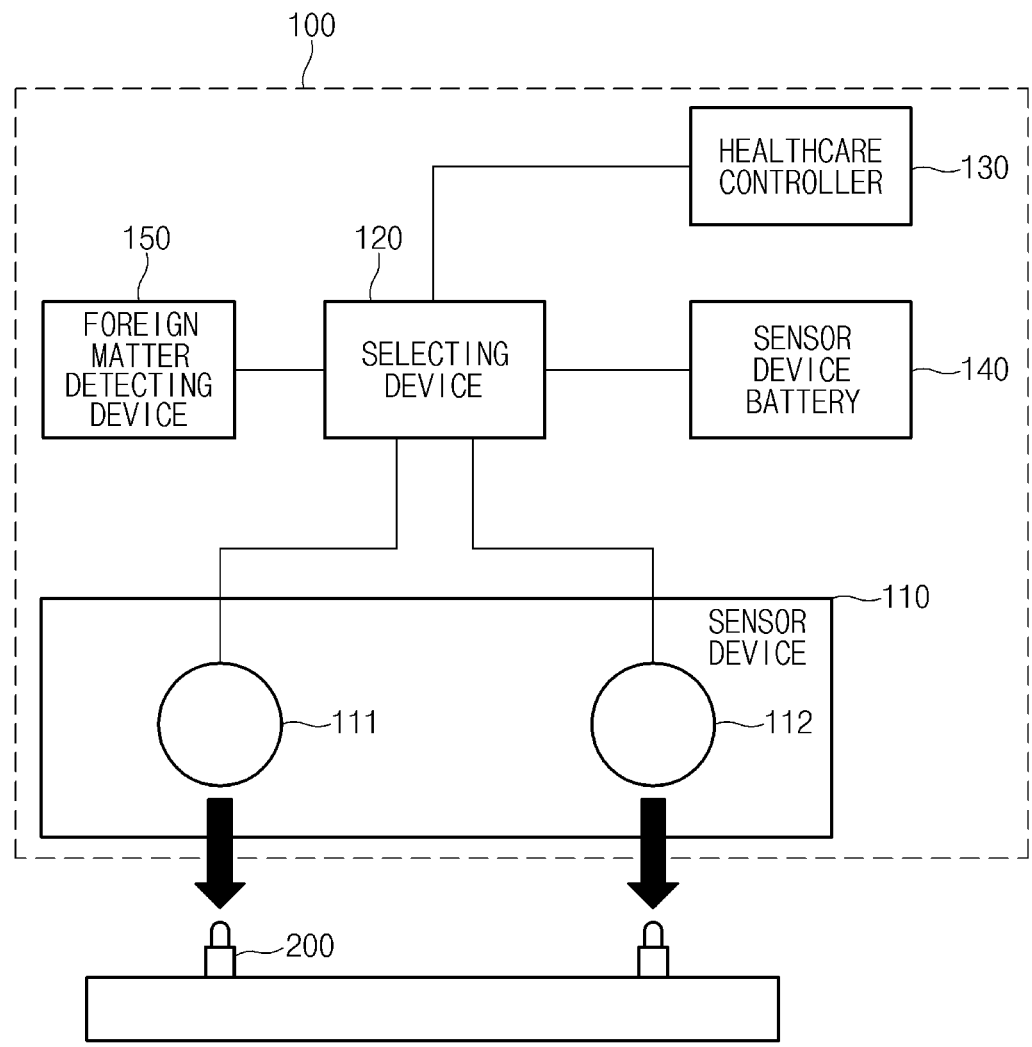
FIG. 1 is a configuration diagram of a healthcare device according to an embodiment of the present disclosure.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Further, the control logic of the present disclosure may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

Hereinafter, embodiments of the present disclosure will be described in detail with reference to the accompanying drawings. In adding the reference numerals to the components of each drawing, it should be noted that the identical or equivalent component is designated by the identical numeral even when they are displayed on other drawings. Further, in describing the embodiment of the present disclosure, a detailed description of well-known features or functions will be ruled out in order not to unnecessarily obscure the gist of the present disclosure.

FIG. 1 is a configuration diagram of a healthcare device according to an embodiment of the present disclosure.

Referring to FIG. 1, a healthcare device 100 according to an embodiment of the present disclosure may include a sensor device 110, a selecting device 120, a healthcare controller 130, a sensor device battery 140, and a foreign matter detecting device 150.

The healthcare device 100 may be a device for measuring a biosignal of a user (for example, a user riding in a vehicle) and may measure the biosignal of the user in a non-contact manner.

The sensor device 110 may include biosignal measuring sensors 111 and 112. A pair of biosignal measuring sensors 111 and 112 may be provided.

The biosignal measuring sensors 111 and 112 may measure various biosignals. Here, measurable biosignals are various types such as electroencephalography (EEG), electrocardiography (ECG), electromyography (EMG), photoplethysmography (PPG), respiration, and electrooculography (EOG).

According to an embodiment of the present disclosure, it will be described as an example that the biosignal measuring sensors 111 and 112 may measure biosignals such as heart rate, heart rate variation, stress, or the like. In addition, description will be given by taking, an example, a case in which the biosignal measuring sensors 111 and 112 according to an embodiment of the present disclosure include electrocardiography (ECG) electrodes.

The biosignal measuring sensors 111 and 112 may be used to measure biosignals or for charging the sensor device 110. That is, when the biosignal measuring sensors 111 and 112 are used to measure the biosignals, the biosignal measuring sensors 111 and 112 may be used as sensors for measuring the biosignals. On the other hand, when the biosignal measuring sensors 111 and 112 are used to charge the sensor device 110, the biosignal measuring sensors 111 and 112 may be used as charging electrodes. Here, when the biosignal measuring sensors 111 and 112 are used to charge the sensor device 110, the electrodes of the biosignal measuring sensors 111 and 112 may be electrically connected to pogo pins 200 outside the healthcare device 100.

The selecting device 120 may selectively connect the biosignal measuring sensors 111 and 112 to the healthcare controller 130 or the sensor device battery 140. In an embodiment of the present disclosure, the selecting device 120 may be implemented with a semiconductor relay, but is not limited thereto.

In other words, the selecting device 120 may connect the biosignal measuring sensors 111 and 112 of the sensor device 110 to the healthcare controller 130 or connect the biosignal measuring sensors 111 and 112 of the sensor device 110 to the sensor device battery 140.

That is, the selecting device 120 may connect the biosignal measuring sensors 111 and 112 to the healthcare controller 130 when the biosignal is measured. The selecting device 120 may connect the biosignal measuring sensors 111 and 112 to the sensor device battery 140 during charging.

According to an embodiment, when charging of the sensor device 110 is completed in a normal state in which the biosignal is not measured, the selecting device 120 may cut off connection between the biosignal measuring sensors 111 and 112, the healthcare controller 130, and the sensor device battery 140, thereby reducing current consumption.

The healthcare controller 130 may collect and calculate a biosignal measured through the biosignal measuring sensors 111 and 112. The healthcare controller 130 may be connected to the biosignal measuring sensors 111 and 112 through the selecting device 120 when measuring the biosignal. In this case, the connection between the biosignal measuring sensors 111 and 112 and the sensor device battery 140 is electrically cut off under the control of the selecting device 120.

The sensor device battery 140 may receive power from the pogo pins 200 through the electrodes of the biosignal measuring sensors 111 and 112 to charge a power supply of the sensor device battery 140. The sensor device battery 140 may be connected to the biosignal measuring sensors 111 and 112 through the selecting device 120 during charging. In this case, the connection between the biosignal measuring sensors 111 and 112 and the healthcare controller 130 may be electrically cut off under the control of the selecting device 120.

The foreign matter detecting device 150 may detect the presence or absence of foreign matter in the healthcare device 100. The foreign matter detecting device 150 may detect foreign matter when it is adsorbed on a display of the healthcare device 100 or the biosignal measuring sensors 111 and 112 during charging.

For example, the foreign matter detecting device 150 may detect whether the foreign matter is adsorbed based on color information of the foreign matter existing on the display. As another example, the foreign matter detecting device 150 may determine whether the foreign matter is adsorbed by determining the reflection amount of an ultrasonic signal. As another example, the foreign matter detecting device 150 may detect whether the foreign matter is adsorbed by comparing a change in current or voltage provided by the selecting device 120 with a preset reference value.

A method for detecting the presence or absence of the foreign matter in the foreign matter detecting device 150 according to an embodiment of the present disclosure may be implemented in various ways, and is not limited to the above embodiments. In addition, the embodiment of the present disclosure has been described as an example in which the foreign matter detecting device 150 is connected to the outside of the selecting device 120. However, the embodiments of the present disclosure are not limited thereto, and the foreign matter detecting device 150 may be located inside the semiconductor relay of the selecting device 120 or anywhere in the healthcare device 100.

In addition, the foreign matter detecting device 150 may display, to the user of the healthcare device 100, a user interface (e.g., warnings), an audio alarm, or a vibration signal indicating that the foreign matter is absorbed.

The pogo pin 200 may have a structure in which a pair of pins protrude and may be electrically connected to the electrodes of the biosignal measuring sensors 111 and 112. The pogo pin 200 may be used to charge the sensor device battery 140 using the biosignal measuring sensors 111 and 112 as charging electrodes.

To charge the healthcare device 100 through the pogo pin 200, a hole which the pogo pin 200 contacts may be separately required in the sensor device 110. However, according to an embodiment of the present disclosure, the biosignal measuring sensors 111 and 112 may be used as charging electrodes, and thus a process for forming a separate hole in the sensor device 110 may not be required. Accordingly, the embodiments of the present disclosure may reduce the cost and size of the healthcare device 100 and improve the aesthetic value.

Figure 2:
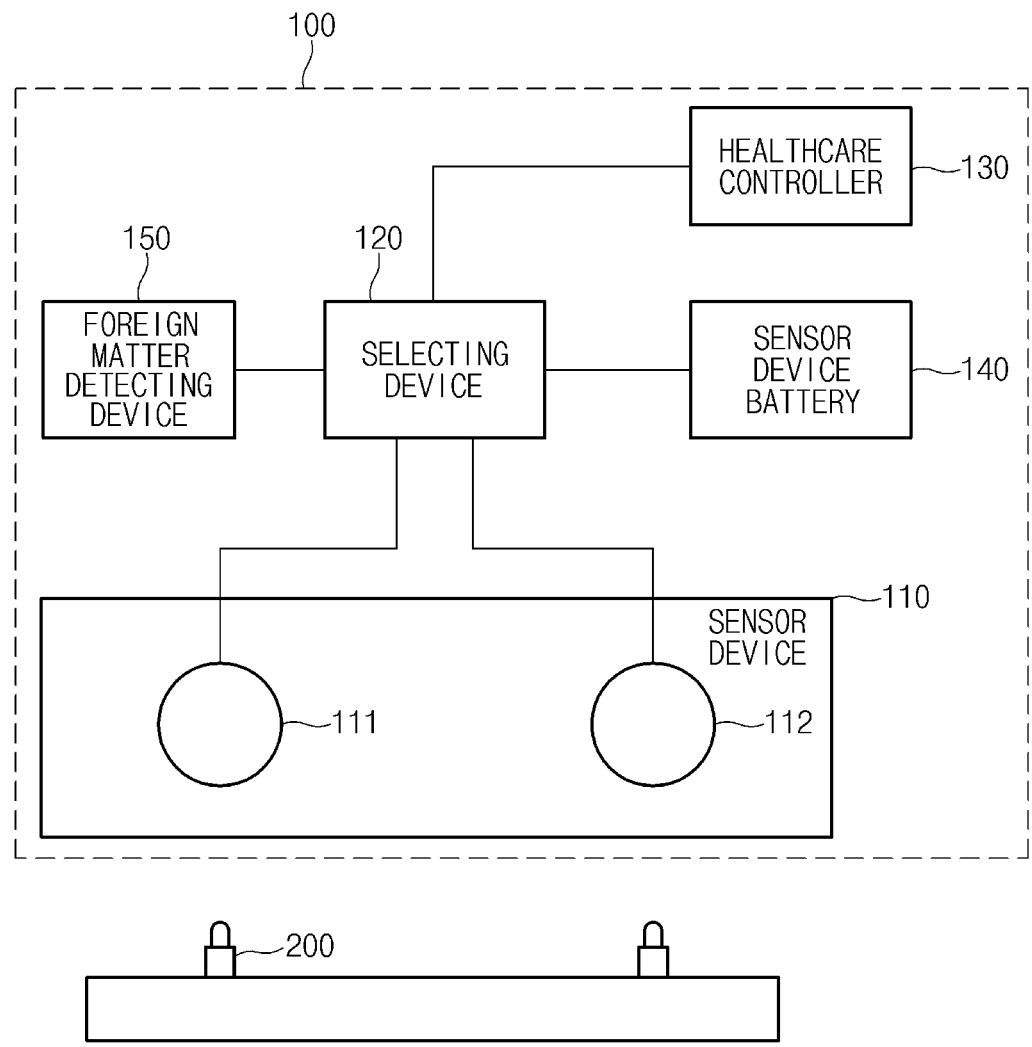
FIGS. 2 and 3 are diagrams for describing operation of the healthcare device of FIG. 1.
Figure 3:
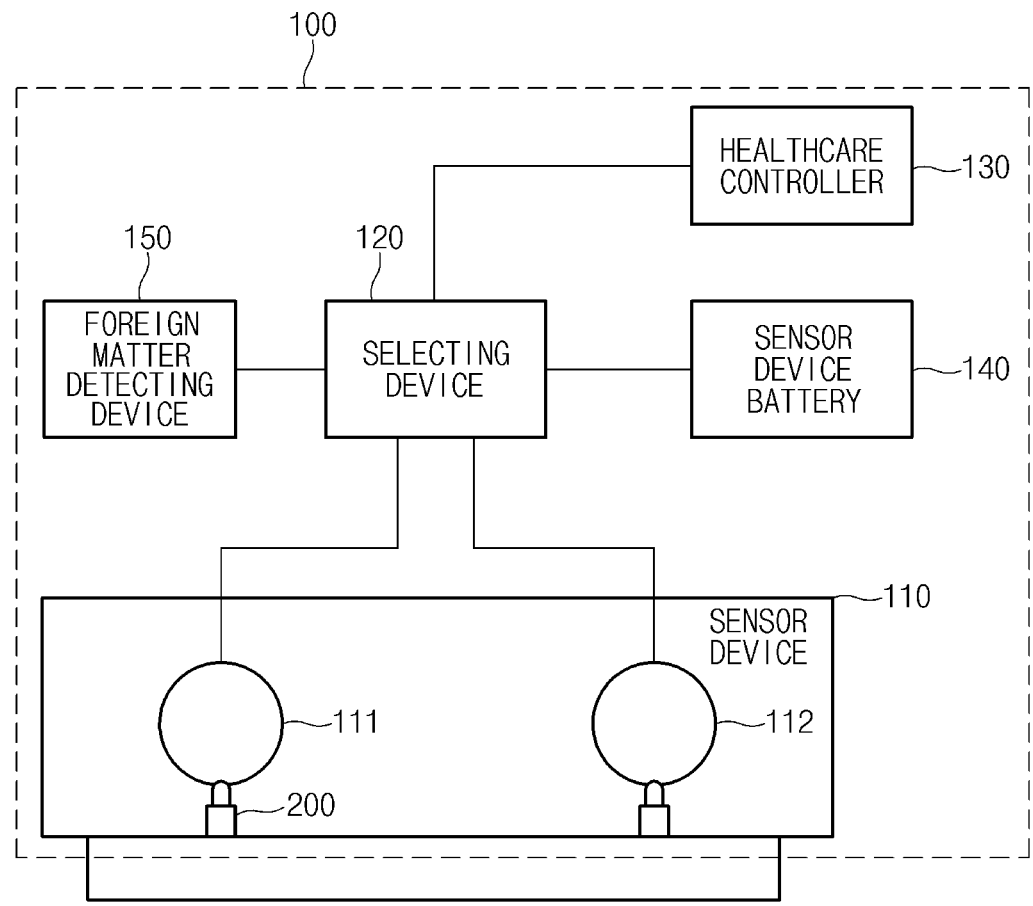

FIGS. 2 and 3 are diagrams for describing operation of the healthcare device 100 of FIG. 1.

It is illustrated in the embodiment of FIG. 2 that the biosignal measuring sensors 111 and 112 are connected to the healthcare controller 130 by the selecting device 120 during the biosignal measurement operation of the healthcare device 100. In this case, because the biosignal measuring sensors 111 and 112 are used as the biosignal measuring sensors, the biosignal measuring sensors 111 and 112 may not be electrically connected to the pogo pin 200.

It is illustrated in the embodiment of FIG. 3 that the biosignal measuring sensors 111 and 112 are connected to the sensor device battery 140 by the selecting device 120 during the charging operation of the healthcare device 100. In this case, the biosignal measuring sensors 111 and 112 may be used as charging electrodes, and thus the pogo pin 200 may be inserted into the sensor device 110. Accordingly, the biosignal measuring sensors 111 and 112 may be electrically connected to the pogo pin 200.

Figure 4:
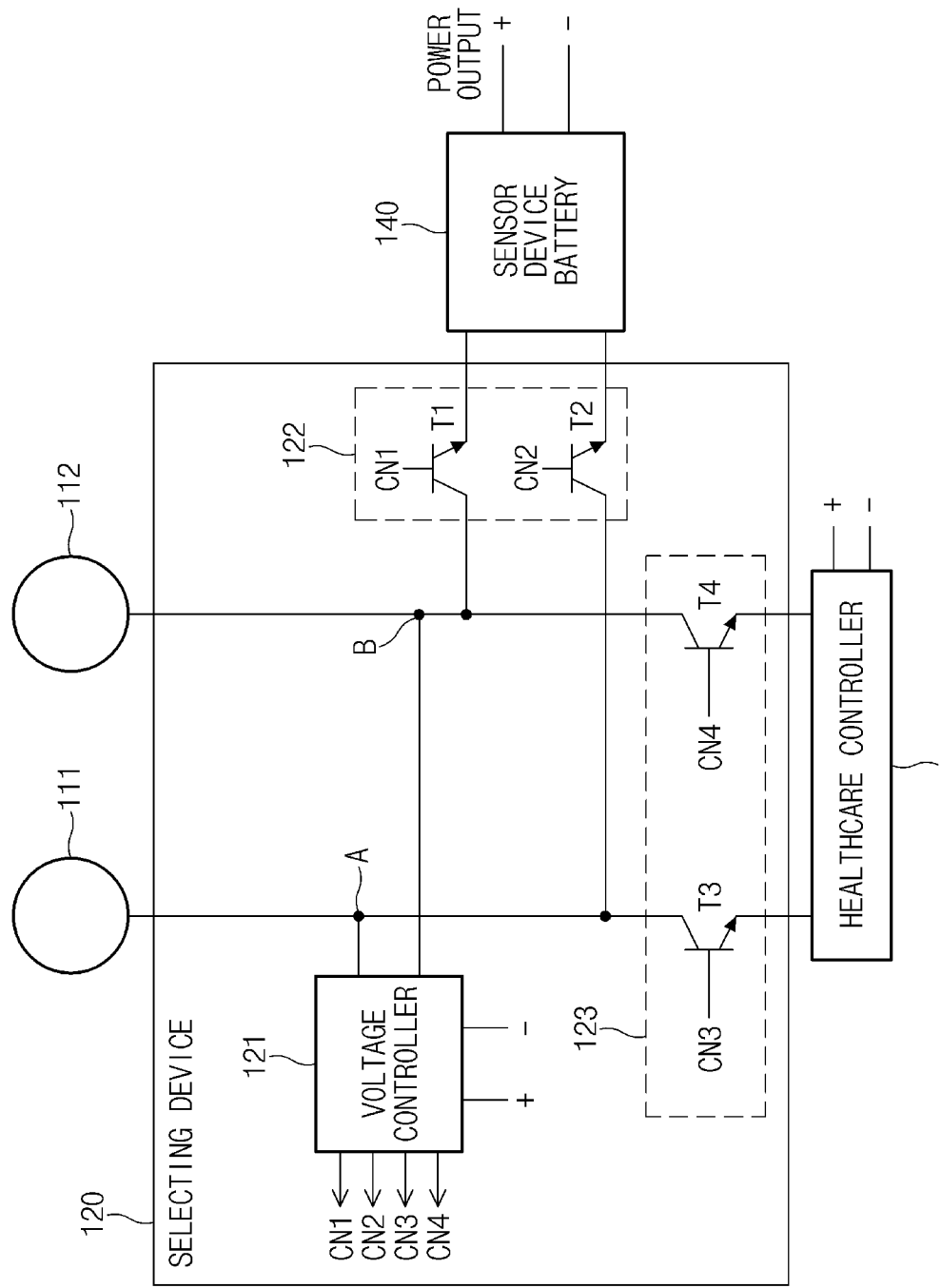
FIG. 4 is a detailed configuration diagram illustrating a selecting device of FIG. 1.

FIG. 4 is a detailed configuration diagram of the selecting device 120 of FIG. 1.

Referring to FIG. 4, the selecting device 120 may include a voltage controller 121, a charge selecting device 122, and a sensor selecting device 123.

The voltage controller 121 may sense voltages of nodes A and B to generate a plurality of control signals CN1 to CN4. Here, the voltage controller 121 may be supplied with driving power from the sensor device battery 140.

For example, the voltage controller 121 may activate a first group of control signals CN1 and CN2 to perform the charging operation when the voltages of the nodes A and B are equal to or higher than a predetermined specific voltage (for example, 5 V). In this case, the voltage controller 121 may control a second group of control signals CN3 and CN4 to be in a deactivated state during the charging operation.

On the other hand, the voltage controller 121 may activate the second group of control signals CN3 and CN4 to perform measurement operation when the voltages of the nodes A and B are less than the predetermined specific voltage. In this case, the voltage controller 121 may control the first group of control signals CN1 and CN2 to be in a deactivated state during the measurement operation.

The charge selecting device 122 may connect the biosignal measuring sensors 111 and 112 and the sensor device battery 140 according to the first group of control signals CN1 and CN2 during the charging operation. That is, when the first group of control signals CN1 and CN2 are activated during the charging operation, the sensor device battery 140 may be connected to the nodes A and B. In this case, the connections between the healthcare controller 130 and nodes A and B may be cut off.

When the first group of control signals CN1 and CN2 are activated during the charging operation, a charging path may be formed such that charging current flows to the sensor device battery 140 through the pogo pin 200, the biosignal measuring sensors 111 and 112, the nodes A and B, and the charge selecting device 122.

The charge selecting device 122 may include switching elements T1 and T2. Here, the switching element T1 may be connected between the node B and the sensor device battery 140, so that switching operation may be controlled in response to the control signal CN1. The switching element T2 may be connected between the node A and the sensor device battery 140, so that switching operation may be controlled in response to the control signal CN2.

The sensor selecting device 123 may connect the biosignal measuring sensors 111 and 112 to the healthcare controller 130 according to the second group of control signals CN3 and CN4 during the biosignal measurement operation. That is, when the second group of control signals CN3 and CN4 are activated during the measurement operation, the healthcare controller 130 may be connected to the nodes A and B. In this case, the connections between the sensor device battery 140 and the nodes A and B may be cut off.

When the second group of control signals CN3 and CN4 are activated during the measurement operation, a measurement path may be formed such that measurement current flows to the healthcare controller 130 through the biosignal measuring sensors 111 and 112, the nodes A and B, and the sensor selecting device 123.

The sensor selecting device 123 may include switching elements T3 and T4. Here, the switching element T3 may be connected between the node A and the healthcare controller 130, so that the switching operation may be controlled in response to the control signal CN3. In addition, the switching element T4 may be connected between the node B and the healthcare controller 130, so that the switching operation may be controlled in response to the control signal CN4.

In an embodiment of the present disclosure, the switching elements T1 to T4 may be implemented with NPN type bipolar junction transistors (BJTs). According to another embodiment, the switching elements T1 to T4 may be implemented with PNP type bipolar junction transistors.

Embodiments of the present disclosure are not limited thereto, and the switching elements T1 to T4 may be implemented with field effect transistors (EFTs). A field effect transistor may include three devices including a source, a drain, and a gate, and it is possible to control the current of the source and the drain by using a principle in which a voltage is applied to a gate electrode, creating a gateway through which electrons flow by an electric field of a channel.

As described above, the selecting device 120 may connect the biosignal measuring sensors 111 and 112 to the healthcare controller 130 or the sensor device battery 140 according to the switching operations of the switching elements T1 to T4.

Table 1 below shows a state in which each of the switching elements T1 to T4 is turned on or turned off according to the potential difference between the nodes A and B during the charging operation or measurement operation.

TABLE 1

| CASE | Potential difference between Nodes A and B | T1 | T2 | T3 | T4 |
|---|---|---|---|---|---|
| Charging | 5 V or more | ON | ON | OFF | OFF |
| Measurement | Less than 5 V | OFF | OFF | ON | ON |
| Charging completion | | OFF | OFF | OFF | OFF |

Referring to Table 1 above, the voltage controller 121 may detect a potential difference between the biosignal measuring sensors 111 and 112, that is, the potential difference between the nodes A and B, as a large potential difference above a specific voltage during the charging operation. The voltage controller 121 may activate the first group of control signals CN1 and CN2 when the potential difference between the nodes A and B is detected above the specific voltage.

When the potential difference between the nodes A and B is equal to or greater than the specific voltage (5 V) during the charging operation, the switching elements T1 and T2 may be turned on and the switching elements T3 and T4 may be turned off in accordance with the first group of control signals CN1 and CN2. Then, it can be seen that the sensor device battery 140 is connected to the biosignal measuring sensors 111 and 112.

On the other hand, the voltage controller 121 may detect the potential difference between the biosignal measuring sensors 111 and 112, that is, the potential difference between the nodes A and B, as a fine potential difference less than the specific voltage when the charging operation is not performed. The voltage controller 121 may activate the second group of control signals CN3 and CN4 when the potential difference between the nodes A and B is detected to be less than the specific voltage.

Accordingly, when the potential difference between the nodes A and B is less than the specific voltage (5 V) during the measurement operation, the switching elements T3 and T4 may be turned on and the switching elements T1 and T2 may be turned off in accordance with the second group of control signals CN3 and CN4. Then, it can be seen that the healthcare controller 130 is connected to the biosignal measuring sensors 111 and 112.

In addition, when charging of the sensor device battery 140 is completed, the voltage controller 121 may deactivate all of the control signals CN1 to CN4. Then, all the switching elements T1 to T4 may be turned off. Accordingly, the connections between the nodes A and B, the sensor device battery 140, and the healthcare controller 130 may be cut off, thereby reducing current consumption.

Figure 5:
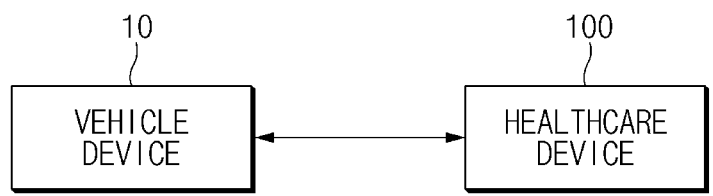
FIG. 5 is a diagram illustrating a vehicle system to which the healthcare device according to an embodiment of the present disclosure is applied.

FIG. 5 is a diagram illustrating a vehicle system to which a healthcare device according to an embodiment of the present disclosure is applied.

Referring to FIG. 5, a vehicle system according to an embodiment of the present disclosure may include a vehicle device 10 and the healthcare device 100 described with reference to FIGS. 1 to 4.

Recently, a vehicle has become a space where a driver may receive various information and services related to traffic and other subject matter while driving as the vehicle accesses the Internet, as well as fulfills a transportation purpose. As a result, the safety and convenience of the driver may be greatly improved, and vehicles may be utilized to obtain and disseminate health care information on a driver and/or passengers occupying a vehicle.

Further, a universal medical service, that is, the healthcare device 100 may be mounted on the vehicle device 10 in addition to a technology related to the driver's safety, thus increasing the driver's safety and convenience.

Here, the healthcare device 100 may provide a healthcare and medical service that may be used remotely for measuring biometric information and obtaining healthcare services, for example, to remotely manage diseases and maintain and improve the health of vehicle occupants. In particular, the healthcare device 100 may acquire a biosignal while the driver of the vehicle is driving the vehicle in an unrestrained state, analyze the driver's health information, feed a result of analysis back to the driver, or transmit the result to the driver's healthcare system.

The vehicle device 10 may be connected to the healthcare device 100 through a communication network to provide information of a user (e.g., a driver) to the healthcare device 100. The healthcare device 100 may receive user information from the vehicle device 10 and recognize a user based on the received user information. The healthcare device 100 may store the measured biosignal information and analyze the stored information to learn the biometric information of the user.

Figure 6:
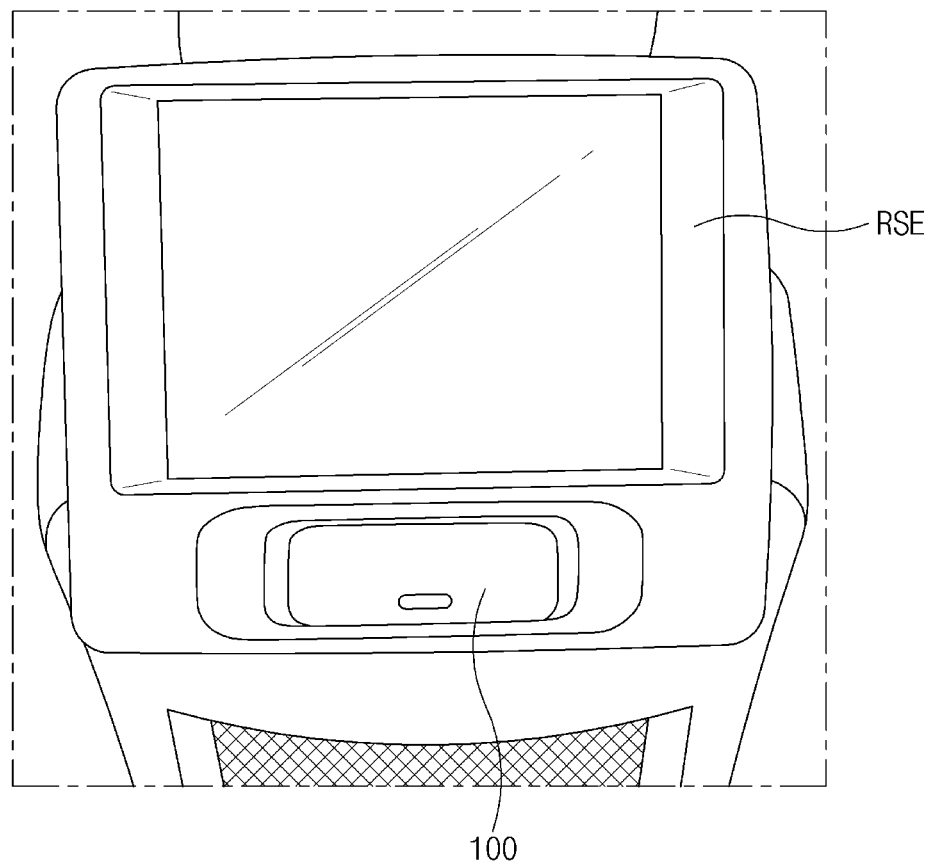
FIGS. 6 and 7 are diagrams for describing the vehicle system of FIG. 5.
Figure 7:
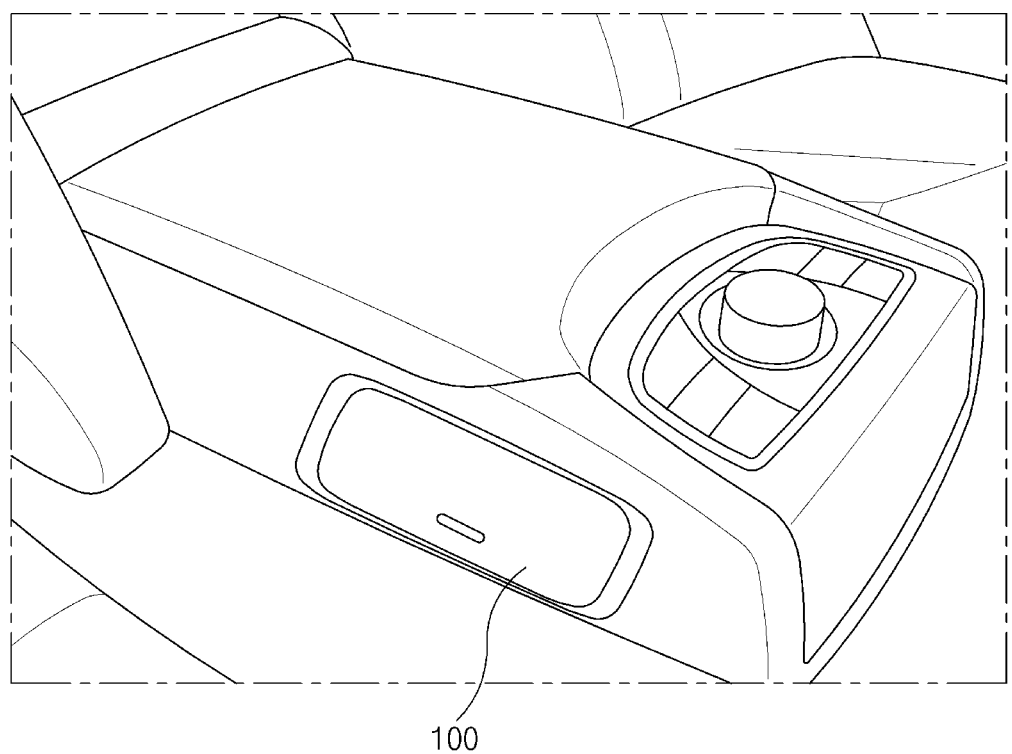

FIGS. 6 and 7 are diagrams for describing the vehicle system of FIG. 5. FIGS. 6 and 7 illustrate that the healthcare device 100 is remotely controlled wirelessly.

The healthcare device 100 according to an embodiment of the present disclosure may be implemented in the interior of the vehicle. In this case, the healthcare device 100 may be integrally formed with internal control units of the vehicle, or may be implemented as a separate device and connected to the control units of the vehicle.

Referring to FIG. 6, the healthcare device 100 according to an embodiment of the present disclosure may be applied to a lower portion of a rear seat entertainment system (RSE). Here, the rear seat entertainment system is 'Wellness Care' technology that measures a biosignal (e.g., stress) of an occupant in the back seat to help change mood.

For example, when the rear seat entertainment system may measure health status information such as stress, a heart rate, and mood to achieve health therapy for mood change when the occupant holds the healthcare device 100 for a specific time (for example, about 1 minute).

As another example, referring to FIG. 7, the healthcare device 100 may be embodied in a recessed structure on the side of the rear armrest of the vehicle or attached through a magnet.

Figure 8:
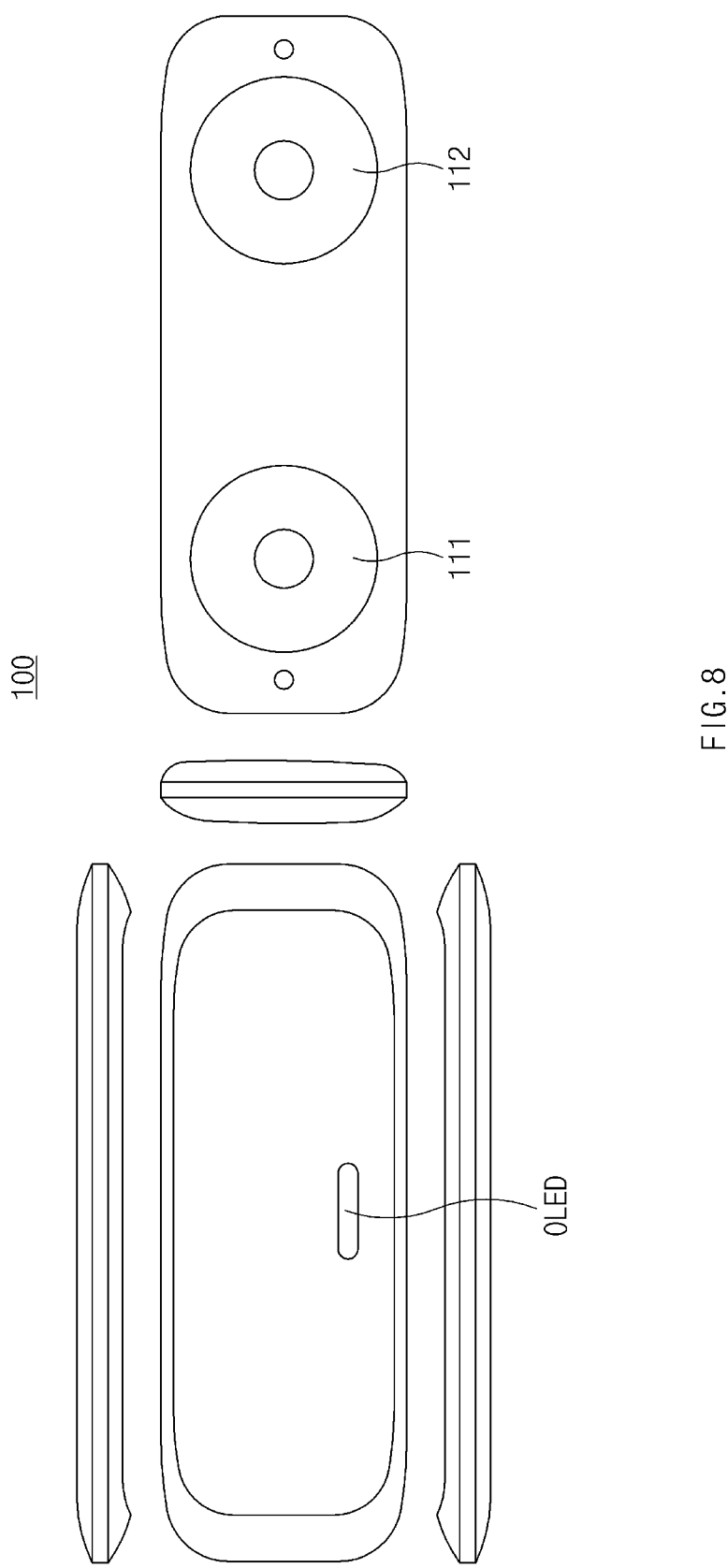
FIG. 8 is a diagram illustrating an example of a healthcare device according to the embodiment of FIGS. 6 and 7.

FIG. 8 is a diagram illustrating an example of the healthcare device 100 according to the embodiment of FIGS. 6 and 7.

Referring to FIG. 8, the healthcare device 100 may include organic light emitting diodes (OLEDs) on the outside. Accordingly, the healthcare device 100 may indicate a charging state, a charging completion state, a current battery state, and a biosignal measurement state of the sensor device through the organic light emitting diodes.

In addition, the healthcare device 100 according to the embodiment of the present disclosure does not have a separate hole connected to the pogo pin 200, and the biosignal measuring sensors 111 and 112 for measuring the biosignal may be exposed to the outside.

Figure 9:
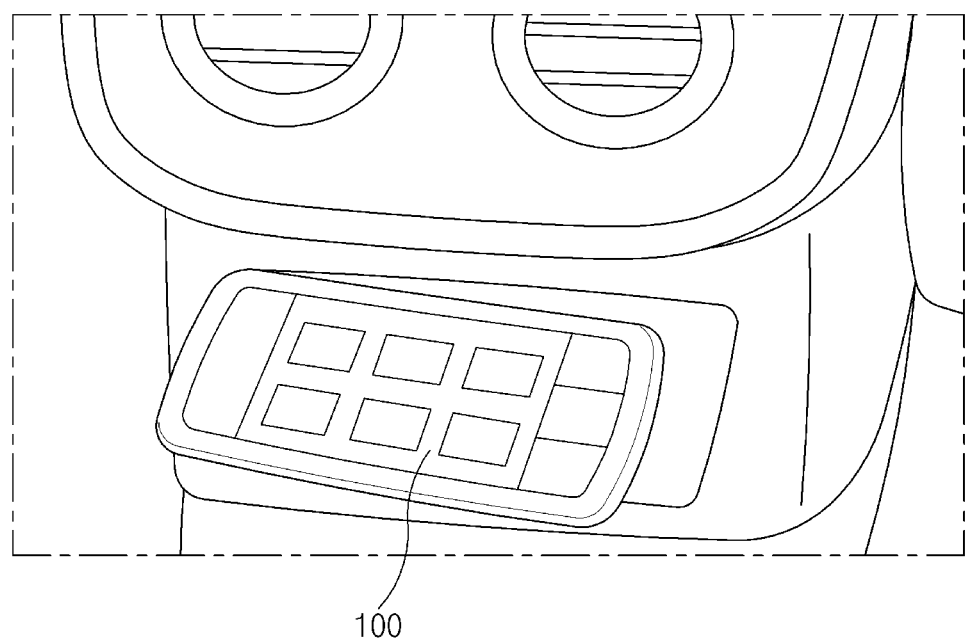
FIGS. 9 and 10 correspond to another embodiment for describing the vehicle system of FIG. 5.
Figure 10:
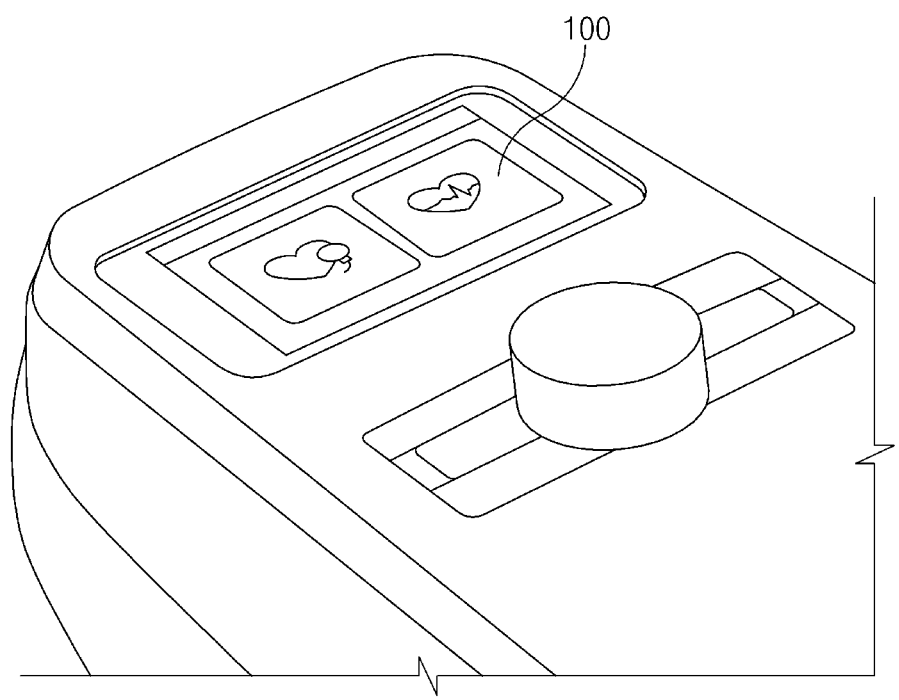

FIGS. 9 and 10 illustrate another embodiment for describing the vehicle system of FIG. 5. FIGS. 9 and 10 illustrate an example in which the healthcare device 100 is implemented in the form of a touch display.

Referring to FIG. 9, it is illustrated that the healthcare device 100 according to an embodiment of the present disclosure is applied to the back of a center console. As another example, referring to FIG. 10, the healthcare device 100 according to an embodiment of the present disclosure may be implemented in a recessed structure on an upper surface of the rear armrest of the vehicle. The pogo pin 200 for charging the healthcare device 100 may be applied to the bottom of the armrest. The healthcare device 100 may link not only a healthcare function but also a seat and an air conditioning control function.

Figure 11:
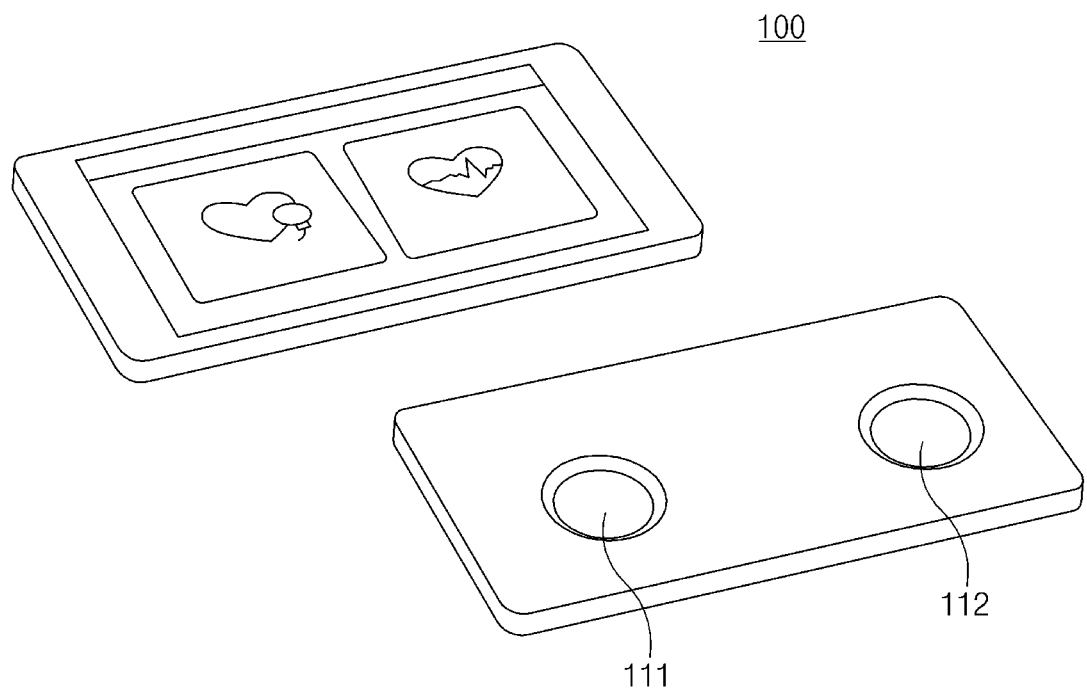
FIGS. 11 and 12 illustrate examples of a healthcare device according to the embodiments of FIGS. 9 and 10.
Figure 12:

FIGS. 11 and 12 illustrate an example of the healthcare device 100 according to the embodiment of FIGS. 9 and 10.

Referring to FIG. 11, the healthcare device 100 may be implemented in the form of a touch display to display a charging state of the sensor device or a biosignal measurement state on a display screen.

In addition, the healthcare device 100 according to the embodiment of the present disclosure does not have a separate hole connected to the pogo pin 200, and the biosignal measuring sensors 111 and 112 for measuring the biosignal may be exposed to the outside.

Referring to FIG. 12, the healthcare device 100 may indicate a charging state (full charged, charging, low battery, contact failure for charging) of the sensor device and the biosignal measurement state through the display screen.

According to the embodiments of the present disclosure, it is possible to reduce the cost and size of the healthcare device and increasing the aesthetic effect by using the biosignal measuring sensor of the healthcare device as a charging electrode.

As those skilled in the art to which the present disclosure pertains may implement the present disclosure in other specific forms without changing the technical spirit or essential features, the foregoing embodiments should be understood as illustrative and not restrictive in all aspects. The scope of the present disclosure is defined by the appended claims rather than the foregoing description and all changes or modifications derived from the spirit and scope of the appended claims and their equivalents should be construed as being included in the scope of the present disclosure.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. A healthcare device, comprising:
 a sensor device provided with a biosignal measuring sensor that measures a biosignal to use the biosignal measuring sensor as a charging electrode during charging;
 a healthcare controller configured to collect and perform calculation on the biosignal measured through the biosignal measuring sensor;
 a sensor device battery configured to receive power from an external pogo pin through an electrode of the biosignal measuring sensor during charging by the charging electrode to charge a power supply of the sensor device battery; and
 a selecting device configured to connect the biosignal measuring sensor to any one of the healthcare controller and the sensor device battery,
 wherein the selecting device includes:
 a voltage controller configured to sense a potential difference between the biosignal measuring sensor and an additional biosignal measuring sensor to control a plurality of control signals;
 a charge selecting device configured to connect the biosignal measuring sensor and the sensor device battery according to a first group of control signals of the plurality of control signals during charging by the charging electrode; and
 a sensor selecting device configured to connect the biosignal measuring sensor and the healthcare controller according to a second group of control signals of the plurality of control signals during measurement of the biosignal.

2. The healthcare device of claim 1, wherein the biosignal measuring sensor includes an electrocardiogram (ECG) electrode.

3. The healthcare device of claim 1, wherein the biosignal measuring sensor is electrically connected to the pogo pin during charging by the charging electrode.

4. The healthcare device of claim 1, wherein the selecting device is implemented with a semiconductor relay.

5. The healthcare device of claim 1, wherein the selecting device connects the biosignal measuring sensor to any one of the healthcare controller and the sensor device battery in correspondence to a potential difference between the biosignal measuring sensor and the additional biosignal measuring sensor.

6. The healthcare device of claim 1, wherein the selecting device connects the biosignal measuring sensor to the healthcare controller during measurement of the biosignal and connects the biosignal measuring sensor to the sensor device battery during charging by the charging electrode.

7. The healthcare device of claim 1, wherein the selecting device cuts off connections between the biosignal measuring sensor, the healthcare controller, and the sensor device battery when measurement of the biosignal and the charging are completed.

8. The healthcare device of claim 1, wherein the voltage controller activates the first group of control signals to perform a charging operation when the potential difference is equal to or greater than a preset specific voltage, and
 activates the second group of control signals to perform a measurement operation when the potential difference is less than the specific voltage.

9. The healthcare device of claim 1, wherein a charge path from the pogo pin to the sensor device battery through the biosignal measuring sensor and the charge selector is formed when the first group of control signals are activated during charging by the charging electrode.

10. The healthcare device of claim 1, wherein the charge selecting device includes switching elements which are connected between the sensor device battery and the biosignal measuring sensor, and of which switching operations are controlled corresponding to the second group of control signals.

11. The healthcare device of claim 1, wherein a measurement path to the healthcare controller through the biosignal measuring sensor and the sensor selecting device is formed when the second group of control signals are activated during charging operation of the biosignal.

12. The healthcare device of claim 1, wherein the sensor selector includes switching elements, which are connected between the biosignal measuring sensor and the healthcare controller and of which switching operations are controlled corresponding to the second group of control signals.

13. The healthcare device of claim 1, further comprising:
 a foreign matter detecting device configured to detect presence or absence of foreign matter of the healthcare device.

14. The healthcare device of claim 13, wherein the foreign matter detecting device displays at least one of a user interface, an audio alarm, or a vibration signal which indicates that the foreign matter is adsorbed to a user of the healthcare device.

\* \* \* \* \*